(12) United States Patent
Rothermel

(10) Patent No.: US 8,612,017 B2
(45) Date of Patent: Dec. 17, 2013

(54) IMPLANTABLE DEVICE

(75) Inventor: Albrecht Rothermel, Neu-Ulm (DE)

(73) Assignee: Retina Implant AG, Reutlingen (DE)

( * ) Notice: Subject to any disclaimer, the term of this patent is extended or adjusted under 35 U.S.C. 154(b) by 1201 days.

(21) Appl. No.: 12/411,268

(22) Filed: Mar. 25, 2009

(65) Prior Publication Data

US 2009/0222063 A1 Sep. 3, 2009

Related U.S. Application Data

(63) Continuation of application No. PCT/EP2007/008045, filed on Sep. 15, 2007.

(30) Foreign Application Priority Data

Sep. 26, 2006 (DE) .......................... 10 2006 047 118

(51) Int. Cl.
*A61N 1/32* (2006.01)
(52) U.S. Cl.
USPC ............ 607/63; 607/2; 607/5; 607/6; 607/65; 607/66; 607/68; 607/72; 607/75; 607/76; 607/53; 607/54
(58) Field of Classification Search
USPC ............................... 607/2, 5, 6, 63–76, 53–54
See application file for complete search history.

(56) References Cited

U.S. PATENT DOCUMENTS

| | | | |
|---|---|---|---|
| 4,232,680 A * | 11/1980 | Hudleson et al. ................ | 607/46 |
| 4,357,497 A * | 11/1982 | Hochmair et al. ................ | 607/5 |
| 4,628,933 A * | 12/1986 | Michelson ....................... | 607/53 |
| 5,024,223 A | 6/1991 | Chow | |
| 5,608,204 A | 3/1997 | Hofflinger et al. | |
| 5,873,901 A | 2/1999 | Wu et al. | |
| 5,895,415 A | 4/1999 | Chow et al. | |
| 6,035,237 A * | 3/2000 | Schulman et al. .............. | 607/63 |
| 6,298,270 B1 | 10/2001 | Nisch et al. | |
| 6,393,327 B1 | 5/2002 | Scribner | |

(Continued)

FOREIGN PATENT DOCUMENTS

| | | |
|---|---|---|
| DE | 42 09 536 | 9/1993 |
| DE | 197 05 988 | 4/1998 |

(Continued)

OTHER PUBLICATIONS

Notice of Reasons for Refusal for Japanese Patent Application No. 2009-529569, mailed Jun. 12, 2012, 10 pages (including English translation).

(Continued)

*Primary Examiner* — Christopher D Koharski
*Assistant Examiner* — Natasha Patel
(74) *Attorney, Agent, or Firm* — Morrison & Foerster LLP

(57) ABSTRACT

An implantable device (10) is used to emit electrical stimulation signals to surrounding tissue by means of at least one stimulation electrode (17). The device (10) has a sensor unit (26), which generates a useful signal (D) in the form of analogue voltage pulses (73) from externally fed signals, and an output stage (28) which generates the stimulation signals (E) from the useful signal (D). The output stage (28) emits the stimulation signals (E) in, averaged over time, a substantially DC voltage free fashion to an external ground (29), which can be connected to the tissue (64).

32 Claims, 7 Drawing Sheets

(56) References Cited

U.S. PATENT DOCUMENTS

| | | | |
|---|---|---|---|
| 6,427,087 B1 | 7/2002 | Chow et al. | |
| 6,458,157 B1 | 10/2002 | Suaning | |
| 6,804,560 B2 | 10/2004 | Nisch et al. | |
| 7,003,354 B2 | 2/2006 | Chow et al. | |
| 7,272,447 B2 | 9/2007 | Stett et al. | |
| 7,979,134 B2 | 7/2011 | Chow et al. | |
| 2001/0031999 A1* | 10/2001 | Carter et al. | 607/69 |
| 2002/0010496 A1 | 1/2002 | Greenberg et al. | |
| 2002/0038134 A1 | 3/2002 | Greenberg et al. | |
| 2002/0091421 A1 | 7/2002 | Greenberg et al. | |
| 2002/0177895 A1 | 11/2002 | Nisch et al. | |
| 2003/0114886 A1* | 6/2003 | Gluckman et al. | 607/2 |
| 2003/0158588 A1 | 8/2003 | Rizzo et al. | |
| 2004/0181265 A1 | 9/2004 | Palanker et al. | |
| 2004/0193232 A1 | 9/2004 | Yagi et al. | |
| 2006/0069416 A1 | 3/2006 | Nisch et al. | |
| 2006/0074461 A1 | 4/2006 | Tano et al. | |
| 2006/0113970 A1 | 6/2006 | Stover et al. | |
| 2011/0238134 A1 | 9/2011 | Chow et al. | |

FOREIGN PATENT DOCUMENTS

| | | |
|---|---|---|
| DE | 199 21 399 | 11/2000 |
| EP | 0 460 320 | 12/1991 |
| EP | 1 239 666 | 9/2002 |
| EP | 1 618 922 | 1/2006 |
| EP | 1 666 002 | 6/2006 |
| EP | 2 289 594 | 3/2011 |
| JP | 2002-325851 | 11/2002 |
| JP | 2002-539859 | 11/2002 |
| JP | 2006-34427 | 2/2006 |
| JP | 2006-517828 | 8/2006 |
| JP | 2007-234643 | 9/2007 |
| JP | 2009-500997 | 1/2009 |
| WO | WO-2004/073547 | 9/2004 |
| WO | WO-2005/000395 | 1/2005 |
| WO | WO-2007/072226 | 6/2007 |

OTHER PUBLICATIONS

Notice of Reasons for Refusal for Japanese Patent Application No. 2009-529570, mailed Apr. 17, 2012, 6 pages (including English translation).
International Preliminary Report on Patentability for PCT/EP2007/008043, mailed on Apr. 22, 2009, 10 pages.
International Preliminary Report on Patentability for PCT/EP2007/008045, mailed on Apr. 22, 2009, 7 pages.
International Search Report for PCT/EP2007/008043, mailed on Apr. 22, 2008, 4 pages.
U.S. Appl. No. 12/410,341, filed Mar. 24, 2009 [Rothermal].
Amendment for U.S. Patent No. 7,979,134 B2, dated Oct. 11, 2010.
Amendment for U.S. Patent No. 7,979,134 B2, dated Jun. 25, 2009.
Notice of Allowance for U.S. Patent No. 7,979,134 B2, dated Mar. 10, 2011.
Office Action for US Publication No. 2011/238134 A1, dated Sep. 1, 2011.
Amendment for US Publication No. 2011/238134 A1, dated Nov. 30, 2011.
Final Office Action for US Publication No. 2011/238134 A1, dated Jan. 31, 2012.
Original claim for U.S. Appl. No. 09/564,841.
Response for European Patent Application No. EP 2 289 594 A1, dated Sep. 2, 2011.
Gekeler et al., "Compound subretinal prostheses with extra-ocular parts designed for human trials: successful long-term implantation in pigs" in Graefe's Arch Clin. Exp. Ophthalmol. (2006).
Humayun et al., Vision Research (1999) 39:2569-2576.
International Search Report for PCT/EP2007/008045, mailed on Oct. 27, 2008, 2 pages.
Jensen and Rizzo, Experimental Eye Research (2006) 1-7.
Jensen et al., Journal of Neural Engineering (2005) 2:S16-S21.
Notice of Reason for Refusal for Japanese Patent Application No. 2009-506960, mailed Jul. 3, 2012, 6 pages (including English translation).
Stelzle et al., "Electrical Properties of Micro-Photodiode Arrays for Use as Artificial Retina Implant," Biomedical Microdevices (2001) 3(2):133-142.
Suaning et al., "An Efficient Multiplexing Method for Addressing Large Numbers of Electrodes in a Visual Neuroprosthesis," Proceedings of the 26th Annual International Conference of the IEEE EMBS, San Francisco, CA, USA, Sep. 1-5, 2004, pp. 4174-4177.
Non-Final Office Action for U.S. Appl. No. 11/305,920 mailed Jun. 6, 2008, 14 pages.
Response to Non-Final Office Action for U.S. Appl. No. 11/305,920 mailed Dec. 4, 2008, 15 pages.
Final Office Action for U.S. Appl. No. 11/305,920 mailed Feb. 19, 2009, 13 pages.
Response to Final Office Action for U.S. Appl. No. 11/305,920 mailed Jun. 17, 2009, 12 pages.
Final Office Action for U.S. Appl. No. 11/305,920 mailed Jul. 2, 2009, 12 pages.
Response to Final Office Action for U.S. Appl. No. 11/305,920 mailed Jan. 4, 2010, 32 pages.
Non-Final Office Action for U.S. Appl. No. 12/298,713 mailed Dec. 6, 2010, 7 pages.
Response to Non-Final Office Action for U.S. Appl. No. 12/298,713 mailed May 6, 2011, 10 pages.
Final Office Action for U.S. Appl. No. 12/298,713 mailed Jul. 25, 2011, 7 pages.
Response to Final Office Action for U.S. Appl. No. 12/298,713 mailed Sep. 23, 2011, 8 pages.
Office Action for U.S. Appl. No. 12/410,341 mailed Aug. 1, 2011, 5 pages.
Response to Non-Final Office Action for U.S. Appl. No. 12/410,341 mailed Dec. 1, 2011, 15 pages.
International Preliminary Report on Patentability for International Application No. PCT/EP2004/005975, 5 pages (undated English translation).
International Search Report for International Patent Application No. PCT/EP2004/005975, mailed Oct. 27, 2004, 3 pages.
International Search Report for International Patent Application No. PCT/EP2007/003576, mailed Sep. 3, 2007, 3 pages.
Written Opinion of the International Searching Authority for International Patent Application PCT/EP2007/003576, issued Oct. 28, 2008, 6 pages.
Office Action for U.S. Patent No. 6,427,087 B1, dated Sep. 20, 2001.
Preliminary Amendment for U.S. Patent 7,003,354 B2, dated Sep. 10, 2002.
Supplemental Preliminary Amendment for U.S. Patent 7,003,354, dated Sep. 11, 2003.
Office Action for U.S. Patent 7,003,354, dated Apr. 8, 2005.
Amendment for U.S. Patent 7,979,134 B2, dated Sep. 9, 2008.
Final Office Action for U.S. Patent No. 7,979,134 B2, dated Jan. 27, 2009.
Office Action for U.S. Patent No. 7,979,134 B2, dated Jul. 30, 2009.
Amendment for U.S. Patent No. 7,979,134 B2, dated Nov. 30, 2009.
Final Office Action for U.S. Patent No. 7,979,134 B2, dated Feb. 18, 2010.
Amendment for U.S. Patent No. 7,979,134 B2, dated May 18, 2010.
Office Action for U.S. Patent No. 7,979,134 B2, dated Jun. 9, 2010.
Lovell et al., "Advances in Retinol Neuroprosthetics," chapter in Handbook of Neural Engineering (ed. M. Akay), John Wiley & Sons, Inc., Hoboken, NJ, USA (2006) 30 pages.
Original claims of U.S. Appl. No. 10/142,277, filed May 9, 2002.
Original claims of U.S. Appl. No. 11/293,871, filed Dec. 2, 2005.
Response for European Patent Application No. 10015489.7 dated Sep. 2, 2011.
Extract from Register of European Patents for EP 2289594, downloaded from register.epo.org Oct. 17, 2013.

\* cited by examiner

IMPLANTABLE DEVICE

RELATED APPLICATION

This is a continuation application of International Patent Application PCT/EP2007/008045, filed Sep. 15, 2007, designating the United States and published in German as WO 2008/037363 A2, which claims priority of German patent application No. 10 2006 047 118.0, filed Sep. 26, 2006. The entire contents of these prior applications are incorporated herein by this reference.

BACKGROUND OF THE INVENTION

1. Field of the Invention

The present invention relates to an implantable device which is used to emit electrical stimulation signals to surrounding tissue by means of at least one stimulation electrode, with a sensor unit that generates, from externally fed signals, a useful signal in the form of analogue voltage pulses, and an output stage, which generates stimulation pulses from the useful signal.

2. Related Prior Art

These days, such devices are often used to support or replace certain physiological functions of the human body or to support sensory perception or, for example, to make sensory perception possible again. By way of example, such devices include, but are not limited to, cardiac pacemakers, cochlear implants or retinal implants.

By way of example, active retinal implants, which are to be implanted into the eye, are provided with a multiplicity of stimulation electrodes, which, to retinal cells that are to be contacted, emit electrical stimulation signals. In the process, a multiplicity of pixels convert incident light into the stimulation signals.

By way of example, such a retinal implant is known from WO 2005/000395 A1, the disclosure of which is hereby explicitly incorporated into the present patent application.

The known retinal implant is used to counteract a loss of sight as a result of retinal degeneration. The basic idea is to implant into the eye of a patient a microelectronic stimulation chip, which replaces the lost sight by electrical excitation of nerve cells.

There are two different approaches for possible designs of such retinal prostheses. The subretinal approach uses a stimulation chip, which is implanted into the subretinal space between the outer retina and the pigment epithelium of the retina, and converts ambient light incident on an array of photodiodes integrated in the stimulation chip into stimulation signals for nerve cells. That is to say this retinal implant stimulates the remaining intact neurons of the degenerated retina, i.e., horizontal cells, bipolar cells, amacrine cells and possibly ganglion cells as well.

Thus, the visual image incident on the array of photodiodes or more complex elements is converted into an electrical stimulation pattern, which then, by the "natural computer", is transmitted to the ganglion cells of the inner retina and from there is lead to the visual cortex via the optic nerve. In other words, the subretinal approach uses the natural interconnections of the once present and now degenerate or lost photoreceptors with the ganglion cells in order to, in the usual way, supply the visual cortex with nerve impulses, which correspond to the visualized image.

By contrast, the epiretinal approach uses a device comprising extra-ocular and intra-ocular parts, which communicate with each other in a suitable fashion. The extra-ocular part comprises a camera and a microelectronic circuit in order to decode received light, that is to say the image information, and to transmit it to the intra-ocular part as a stimulation pattern. The intra-ocular part comprises an electrode array which contacts the neurones of the inner retina and hence directly stimulates the ganglion cells located there.

While the subretinal approach pursues the transmission of light and stimulation of the retina in situ, the image information in the case of the epiretinal approach has to be converted outside into a spatial and temporal stimulation pattern of electrical pulses so that these can be "understood" by the visual cortex.

It is known from a number of publications that transmitting stimulation signals from the stimulation electrodes to the contacted cells requires particular attention. This is due to the fact that the coupling between a stimulation electrode and the contacted tissue is of a capacitive nature; hence, it is only possible to use transient signals for the stimulation. This capacitive coupling is due to the fact that a capacitance (Helmholtz double layer) is formed at the boundary between the electrode and electrolyte in the eye as a result of the electrode polarization.

In the case of the subretinal implant in accordance with WO 2005/000395, mentioned at the outset, the incident light is therefore converted into monophasic anodic voltage pulses with a pulse duration of approximately 500 microseconds and a pulse spacing of preferably 50 ms so that this results in a repetition frequency of 20 Hz, which was found to be sufficient for flicker-free sight and also corresponds to the physiological flicker frequency in the case of low ambient brightness.

Thereby, the pulse spacing of the order of 50 ms is sufficient to be able to reset the electrode polarization. After the stimulation current, which is fed into the tissue by the respective anodic voltage pulse, is emitted, the output of the implant is connected to the electrical ground of the implant by a short-circuit switch so that the capacitance of the Helmholtz double layer discharges again and, averaged over time, there is virtually no charge transport into the tissue.

Humayun, et al., "Pattern Electrical Stimulation of the Human Retina", *Vision Research* 39 (1999) 2569-2576, report experiments with epiretinal stimulation, in which so-called biphasic pulses are used which have a cathodic phase, an intermediate phase and an anodic phase of respectively 2 milliseconds. In the case of a stimulation frequency of between 40 and 50 Hz, i.e., significantly above the physiological flicker frequency, flicker-free perception could be observed in two patients.

Jensen, et al., "Responses of Rabbit Retinal Ganglion Cells to Electrical Stimulation with an Epiretinal Electrode", *J. Neural Eng.* 2 (2005) 16-21, report the epiretinal excitation of ganglion cells in a rabbit. In the case of anodic and cathodic current pulses lasting 1 millisecond, the authors observed an average latency of the ganglion cells of between 11 and 25 milliseconds for the excitation on the inner retina.

Jensen and Rizzo, "Thresholds for Activation of Rabbit Retinal Ganglion Cells with a Subretinal Electrode", *Experimental Eye Research* 2006, 1-7, report subretinal stimulation experiments on an isolated rabbit retina using monophasic current pulses lasting between 0.1 milliseconds and 50 milliseconds, in which they observed latencies of approximately 25 milliseconds.

However, at present, it is not possible to obtain the energy for generating the electrical stimulation signals from the incident useful light itself, even in the case of subretinal implants, so that additional external energy is required. Whereas implants without cables, whose energy is supplied by a co-implanted battery, have been available for quite some time in the case of cardiac pacemakers, many other implants, such as both retinal implants and cochlear implants, require a permanent external supply of energy due to their smaller dimensions and physiological limitations.

In the case of retinal implants, this external energy is either fed by additionally irradiated, non-visible light or it is coupled-in inductively from outside by a coil for example, or it is supplied by means of a cable.

The implant known from WO 2005/000395 A1 is therefore wirelessly supplied with electrical energy by irradiated IR light or by inductively coupled-in RF energy, with it being possible that information for controlling the implant is contained in this externally fed external energy.

US 2004/0181265 A1 discloses a retinal implant which is operated by ambient light only, and which does not use external components for either the energy supply or the provision of image information. The known implant comprises an implanted field of photovoltaic cells, which react to ambient light and generate a supply voltage for a likewise implanted stimulation chip and which are connected to said chip via a cable running within the eye.

The stimulation chip comprises a number of pixels which each have a light sensitive circuit and an electrode connected thereto. The retinal cells are stimulated by means of this electrode using biphasic pulses, which have a pulse duration of 1 ms and a repetition rate of 25 Hz. The biphasic pulses shall be designed in such a way, that, averaged over time, they do not transport charge into the surrounding tissue.

However, since wireless retinal implants for human applications with a sufficient quality are currently not yet available, it is not only epiretinal but also subretinal implants which are currently being used, with the required external energy being supplied to the latter by means of cables.

Gekeler, et al., "Compound subretinal prostheses with extra-ocular parts designed for human trials: successful long-term implantation in pigs", *Graefe's Arch Clin Exp Opthalmol* (28 Apr. 2006) [Epub ahead of print], describe, for example, a subretinal retinal implant in which the external energy and the control signals are fed to the chip implanted in the eye via a cable.

Since, on the one hand, DC voltage operated integrated circuits are generally present on the implants, and, on the other hand, since there is little space available on the implants themselves, the known implants are supplied directly with DC voltage. In the case of a supply with AC voltage, the rectifiers needed on the implant would require too much space, particularly due to the necessary smoothing capacitors, and could not be implemented in integrated circuits in a technically sensible fashion either. These problems occur in subretinal retinal implants in particular, but other implants must, of course, also be designed in a space-saving fashion.

However, in the long term, the supply of DC voltage via a cable leads to electrolytic decay processes in the tissue surrounding the cable so that this type of supply of external energy to implants is not satisfactory either.

SUMMARY OF THE INVENTION

In view of the above, it is an object of the present invention to improve, with the device mentioned at the outset, the emission of stimulation signals, preferably by using simple circuitry.

According to the invention, this and other objects are achieved in the case of the device mentioned at the outset in that the output stage emits the stimulation signals in, averaged over time, a substantially DC voltage free fashion to an external ground, which can be connected to the tissue.

The object underlying the invention is completely achieved in this way.

That is to say, the inventors of the present application have recognized that the electrolytic decay processes in the surrounding tissue should be avoided not only in the region of the cables supplying the supply voltage, but also in the region of the stimulation electrodes.

Although the biphasic design of the stimulation current, such that on average there is no charge transport into the tissues, is already known from the WO 2005/00395 A1, mentioned at the outset, the known retinal implant does not have, averaged over time, a DC voltage free stimulation, for which, according to the invention, provision is now made.

In this case, it is advantageous that DC voltage free stimulation pulses are emitted independently of the type of electrical supply, that is to say also in the case of wirelessly supplied implants.

According to a further object the device has a DC supply voltage and an electrical ground which are substantially symmetric with respect to an external ground, whereby preferably the output stage comprises an inverter which supplies the stimulation signals to the stimulation electrode as a sequence of pulses which respectively have two different phases.

An advantage of this measure is that the stimulation signals can, averaged over time, be emitted in a DC voltage free fashion with respect to the external ground using simple circuitry, because a negative voltage is now supplied to the chip with respect to the external ground, i.e., the patient.

Here, the inverter provides a possibility for reversing the polarity of the voltage pulses using simple circuitry. As a result of the biphasic stimulation signals which are symmetric with respect to the external ground, it is already free from the DC voltage after a very short period of time. It is only during this period of time that there are successive voltages which could effect an electrolytic decay; however, an inverse voltage pulse is already emitted within the short period of time of the biphasic pulse.

According to another object the inverter has two branches, connected in parallel to one another, between the output of the sensor unit and the stimulation electrode, both branches respectively comprising at their output a first current mirror connected to a first substantially square AC voltage and with the one branch comprising a second current mirror, connected to a second substantially square AC voltage, which is connected between the sensor unit and the first current mirror.

This measure is advantageous in particular in terms of the circuitry because it provides an elegant solution for the pole reversal of the voltage pulses and it simultaneously exhibits a very low current intake, especially, since the inverter can be controlled by the phase changes of the square AC voltages.

According to a still further object the inverter reverses the polarity of the voltage pulses with respect to the external ground synchronously with the AC voltages.

An advantage of this measure is that the pole reversal of the external AC voltages which is effected from outside and is present in any case can simultaneously be used to reverse the polarity of the voltage pulses with respect to the external ground. This results in, averaged over time, DC voltage free excitation impulses with respect to the external ground.

However, it is also possible to effect the pole reversal by control signals which are generated on the chip or supplied from the outside.

It is another object that the device comprises an input stage which can be connected to a supply unit by means of which the device is supplied with electrical energy, whereby the supply unit is connected to the device via cables by means of which it supplies the input stage with at least one substantially square electrical AC voltage which is, averaged over time, at least virtually free of a DC voltage with respect to an external ground, which can be connected to the tissue.

An advantage of this measure is that also the supply of the novel device is, averaged over time, at least virtually free of a DC voltage.

That is to say, the inventors of the present application have recognized that it is neither necessary to supply the implant with DC voltage, nor that an AC voltage supply with a corresponding rectification is required on the implant. Rather, if a substantially square electrical AC voltage is fed as the supply, then the potential level can be selected such that the supply voltage, averaged over time, is at least virtually free of DC voltage. The troublesome electrolytic decay processes are at least for the large part avoided in this fashion, on the supply side as well.

It is for this reason that a square AC voltage is supplied to the implant (also referred to as a chip) which has now to be converted into a DC supply voltage. In the simplest case, this is already made possible by virtue of the fact that only the positive pulses or "half-waves" are used as the DC supply voltage; this leads to a type of pulsing DC voltage which does not, however, have to be smoothed by capacitors. By way of example, in the case of correspondingly longer pulse durations of several hundred milliseconds, it is possible in each case to switch off the circuits on the chip synchronously with the positive voltage pulses. On the other hand, it is possible to ensure that the negative half-waves of the external square AC current are, so to speak, folded upwards as well by using simple changeover switches or inverters, as is also possible, for example, by using bridge rectifiers.

Although the DC supply voltage in this case still comprises voltage pulses, with small voltage gaps occurring between said pulses due to the finite pulse-edge gradient during the change of polarity, such a pulsed DC supply voltage can however be used for the electrical supply of the implants in particular if—as mentioned above—the electronics are in each case switched off during the voltage gaps or voltage drops, which, in the simplest case, can be achieved by in each case switching off the DC supply voltage at the output of the corresponding rectifier.

In other words, using a virtually square AC voltage as the electrical supply in accordance with the invention affords the possibility of designing the input stage in a space-saving fashion since no smoothing or stabilizing is required on the chip.

On the other hand, if required, a possibly desired smoothing can be achieved by using the parasitic capacitances present on the chip in any case if the switchover time is short enough and the current intake is small enough during this time.

According to another object the supply unit supplies the input stage with at least two substantially square electrical AC voltages, which are, averaged over time, at least virtually free of a DC voltage with respect to the external ground, with the AC voltages being phase-shifted with respect to one another.

An advantage of this measure is that the voltage drops or gaps occurring when one of the two AC voltages is rectified can be compensated for by the other AC voltage as a result of the phase-shift. Using a simple circuitry, it is then possible to provide a constant or at least virtually constant DC supply voltage without using capacitors, with the electrical energy supplied by a cable, averaged over time, being DC voltage free.

According to a further object, the input stage comprises a rectifier circuit which rectifies the AC voltages and adds them to form a DC supply voltage.

An advantage in this case is that the amplitudes of the two square AC voltages themselves each only have to be approximately half the size of the actually required DC supply voltage. For example, if the two supply voltages have a pulse sequence of +1.5 V and −1.5 V with respect to the external ground, a DC supply voltage of 3 V with respect to the electrical ground on the chip can be generated there.

The smaller voltage steps of the two AC voltages have the additional advantage that in addition to the, averaged over time, DC voltage free supply, the applied voltages, which could effect electrolytic decay, are also low.

It is a still further object that the input stage is supplied with a first and a second AC voltage which, while exhibiting approximately the same curve profile and approximately the same amplitudes, are at least virtually inverted with respect to one another.

An advantage of this measure is that the rectifier circuit can have a very simple design because the externally supplied square AC voltage is symmetric, and hence comparable or mirrored circuits can be used to rectify the two AC voltages.

As mentioned above, these two AC voltages can then also be used to control reversing of the inverted rectifier provided at the output of the implant.

Furthermore, it is an object that the rectifier circuit generates the DC supply voltage from the first and the second AC voltages such that the electrical ground thereof and the DC supply voltage are symmetric with respect to the external ground.

This measure makes a very simple rectification of the externally supplied voltages possible, with in each case the negative pulses then being connected to the electrical ground, and the positive pulses being connected to the DC supply voltage by means of the rectifier circuit. The symmetry with respect to the external ground then is a result of the two square AC voltages respectively being symmetric with respect to the external ground.

In this context, it is then preferable for the rectifier circuit to have switches for the respective AC voltage which are actuated by the respective other AC voltage.

This measure makes a very simple design of the rectifier circuit possible; the positive pulses of the two DC voltages are respectively switched to the DC supply voltage in accordance to their phase offset with respect to one another, with the then respectively negative pulses of the other AC voltage being used to actuate the switches. The respective negative pulses of the AC voltages are switched to the electrical ground in the same fashion, with the corresponding switches being actuated by the positive pulses of the respective other AC voltage.

In this context, it is then preferable for the rectifier circuit to comprise two branches with respectively two field-effect transistors connected in parallel at their output electrodes, with the output electrodes in the first branch forming the electrical ground and the output electrodes in the second branch emitting the DC supply voltage, and with every field-effect transistor being connected to one of the two AC voltages at its input electrode and being connected to the other one of the two AC voltages at its control electrode.

This measure is a technologically particularly simple and sensible implementation of the rectification described above, with one AC voltage respectively being switched by the other AC voltage. In this case, field-effect transistors are used as switches which, on the one hand, only have a very low power consumption and, on the other hand, have a very low forward voltage with respect to the conventional rectifier diodes. This makes it possible to build up a virtually continually constant DC supply voltage from the two square AC voltages which are phase-shifted by 180° with respect to one another; voltage drops are generated only at the pulse-edge transitions of the pulses.

In order to counteract this problem, it is furthermore preferable for the output of the second branch to be connected to the DC supply voltage via a switch which is always open when the AC voltages change their polarity with respect to the external ground.

As already mentioned above, this makes it possible to provide a constant DC supply voltage, while keeping very short the duration of the switch being kept open.

The small gaps in the voltage can, on the other hand, be compensated for by, for example, supplying the input stage with a second pair of substantially square AC voltages which are inverted with respect to one another and which are phase-shifted with respect to the first pair, with this phase-shift not equalling 180°. Superposing these DC supply voltages generated by these two pairs of AC voltages can generate a temporally constant DC voltage without voltage drops.

It is another object that the or every AC voltage has a trapezoidal voltage profile with top phases of constant voltage and short pulse-edge phases in which the polarity with respect to the external ground changes, with the duration of the top phases being of the order of at most 100 ms, and the pulse-edge phases preferably being at most 10%, preferably being less than 1% but more than 0.05% of the top phase.

An advantage of this measure is that extremely steep pulse edges, which can lead to RF interference in appropriate rectification, are not used and that the duration of the top phases is matched to the repetition frequency at which the stimulation impulses can be emitted to the tissue for physiological reasons.

In principle, in the first instance, arbitrary top phases, pulse-edge phases and repetition frequencies are possible; from a purely electronic point of view, it is also possible to process substantially shorter or substantially longer pulses than the pulses between 5 ms and 100 ms relevant here.

However, it was confirmed by experiments that the above-mentioned orders of magnitude are sensible, particularly in the case of retinal implants.

This is due to the fact that scientists of the applicant sub-retinally implanted an active retinal implant of the type mentioned at the outset into two informed patients, following a protocol approved by the responsible ethics commission, and investigated, inter alia, what influence different repetition frequencies and pulse durations have on the visual perception. For this purpose, the implant was equipped with a matrix of electrodes which were to be stimulated directly and which were separated by a distance of 280 micrometers with respect to one another. Pulse shape, pulse duration and pulse repetition frequency could be adjusted individually using external electronics.

In the process, the retina of a blind patient was stimulated subretinally by electrodes using biphasic, anodically commencing pulses lasting up to 4 ms. When different repetition frequencies were applied, that is to say when the stimulation used a sequence of "flashes" with a certain frequency, the following observation was made regarding the perception of the patients:

In the case of higher frequencies above approximately 10 Hz, the patient only perceived the flashes for a little while; after this the subjective perception of the flashes disappeared.

By contrast, in the case of electrical stimulation using an average frequency below 10 Hz, the stimulation impulses were perceived as separate flashes over at least a couple of seconds. By contrast, in the case of frequencies of a few Hz and below, each flash was perceived as an individual flash, and the perception remained stable even over a period of minutes.

Hence, if the repetition frequency of the pulses in the approximately square AC voltages corresponds to the repetition frequency of the stimulation pulses, it is possible to directly derive the control signals from the AC voltage.

Furthermore, it is preferable for the sensor unit to have an output amplifier at its output, the output of which is always switched off by means of a control signal when the AC voltage changes its polarity with respect to the external ground.

This method is also advantageous in terms of the circuitry because the output pulse of the sensor unit is converted so to speak into two pulses which are symmetric with respect to the pulse edges of the AC voltages, with now only one of two the pulses having to have its polarity reversed in order to obtain excitation pulses which are, averaged over time, emitted in a DC voltage free fashion.

Finally, it is preferable for the inverter to have a switch at its output, which always briefly connects the output to the external ground when a voltage pulse is over, the amplitude of which thus being connected to the internal ground for the duration of the pulse spacing.

An advantage of this method is that the Helmholtz capacitance on the stimulation electrode, charged by the voltage pulse, quickly discharges again, as is already known, in principle, from WO 2005/000395 A1, mentioned at the outset.

Finally, it is an object that the device is an active retinal implant, the sensor unit of which comprising a multiplicity of image cells which convert incident light into electrical signals, with the sensor unit using the electrical signals to generate the payload or useful signal in the form of analogue voltage pulses of a certain pulse duration and certain pulse spacing, the amplitudes of which depending on the respective intensity of the incident light.

This measure is already known from the WO 2005/000395 A1, mentioned at the outset, so that reference may be made to this citation with regard to the advantages related thereto.

Further advantages result from the description and the appended drawing.

It is understood that the features mentioned above and the features which are still to be mentioned below can be used not only in the respectively specified combination, but also in other combinations or on their own, without departing from the scope of the present invention.

BRIEF DESCRIPTION OF THE DRAWINGS

An embodiment of the invention will be explained in more detail in the following description and is illustrated in the drawing, in which.

DETAILED DESCRIPTION OF A PREFERRED EMBODIMENT

Figure 1:
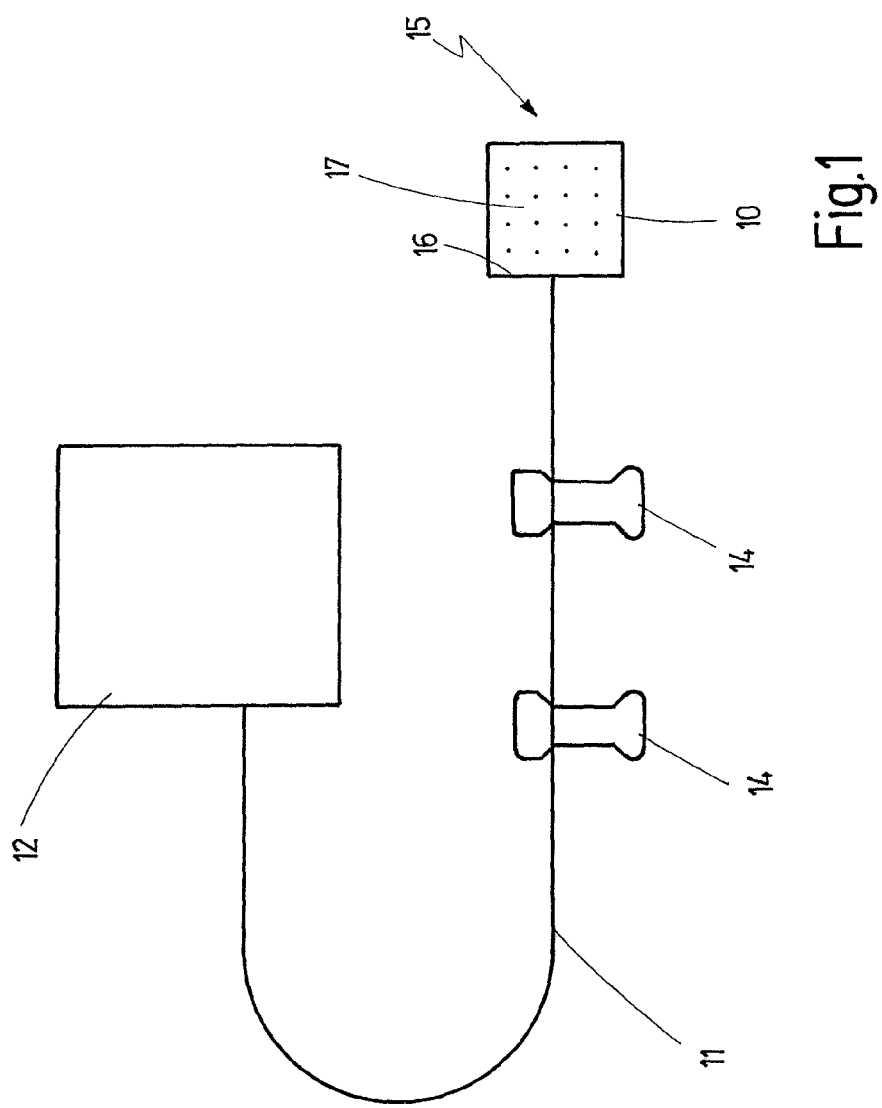
FIG. 1 shows a schematic representation of an implantable device, in this case a retinal implant, which representation is not drawn to scale.

FIG. 1 schematically illustrates an implantable device 10, with the dimensions not being reproduced to scale. A cable 11 is used to connect the device 10 to a supply unit 12 which supplies electrical energy and control signals to said device 10. Attachment lugs 14 are provided on the cable 11 by means of which said cable can be attached to the body of the person into whom the implant 10 will be implanted.

The device 10 can be any implant by means of which nerve cells are excited. In the case shown, it is an active retinal implant 15 which has a film 16 as a carrier on which stimulation electrodes 17 for emitting stimulation signals to nerve cells are arranged.

Figure 2:
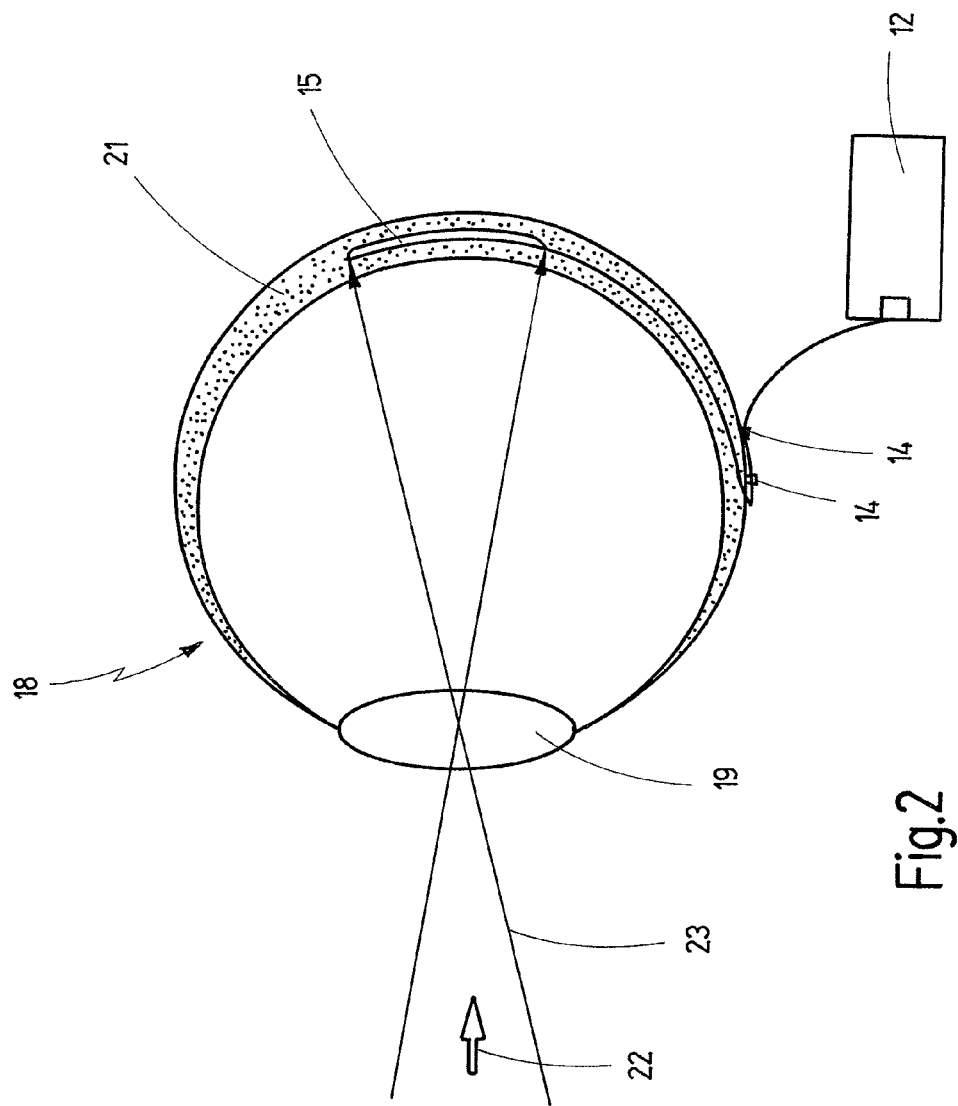
FIG. 2 shows a schematic representation of a human eye, likewise not to scale, into which the retinal implant according to FIG. 1 is inserted.

The retinal implant 15 according to FIG. 1 is designed to be implanted into a human eye 18, the latter being illustrated very schematically in FIG. 2. For the purposes of simplicity, only the lens 19 and the retina 21, into which the implant 15 was implanted, are shown. Thereby, the implant 15 is preferably inserted into the so-called subretinal space which forms between the pigment epithelium and the photoreceptor layer. In case the photoreceptor layer is degenerated or lost, the subretinal space forms between the pigment epithelium and the layer of bipolar cells and horizontal cells. In the process, the retinal implant 15 is placed such that stimulation signals can be imparted onto the cells in the retina 21 using the stimulation electrodes 17, as shown in FIG. 1.

Visible light, which is indicated by an arrow 22 and the beam path of which can be seen at 23, is guided via the lens 19 to the implant 15, where the visible light 2 is converted into electrical signals which are in turn changed into stimulation signals.

It can be seen that the cable 11 is led out of the eye on the side and is attached there on the outside to the sclera using attachment lugs 14 before the cable continues to lead to the external supply unit 12.

The supply unit 12 is then attached outside of the eye, for example, to the cranium of the patient, in a fashion which is not illustrated in any more detail. Electrical energy is sent to the implant 10 from the supply unit 12, with it being possible to simultaneously send control signals which influence the functioning of the implant as is described, for example, in WO 2005/000395 A1, mentioned at the outset, the content of which is hereby fully incorporated into the subject matter of the present application.

It should also be mentioned that in FIGS. 1 and 2 the dimensions of in particular the retinal implant 15, the attachment lugs 14 and the external supply unit 12 are illustrated neither to scale nor in the correct dimensional relationship with respect to one another.

Figure 3:
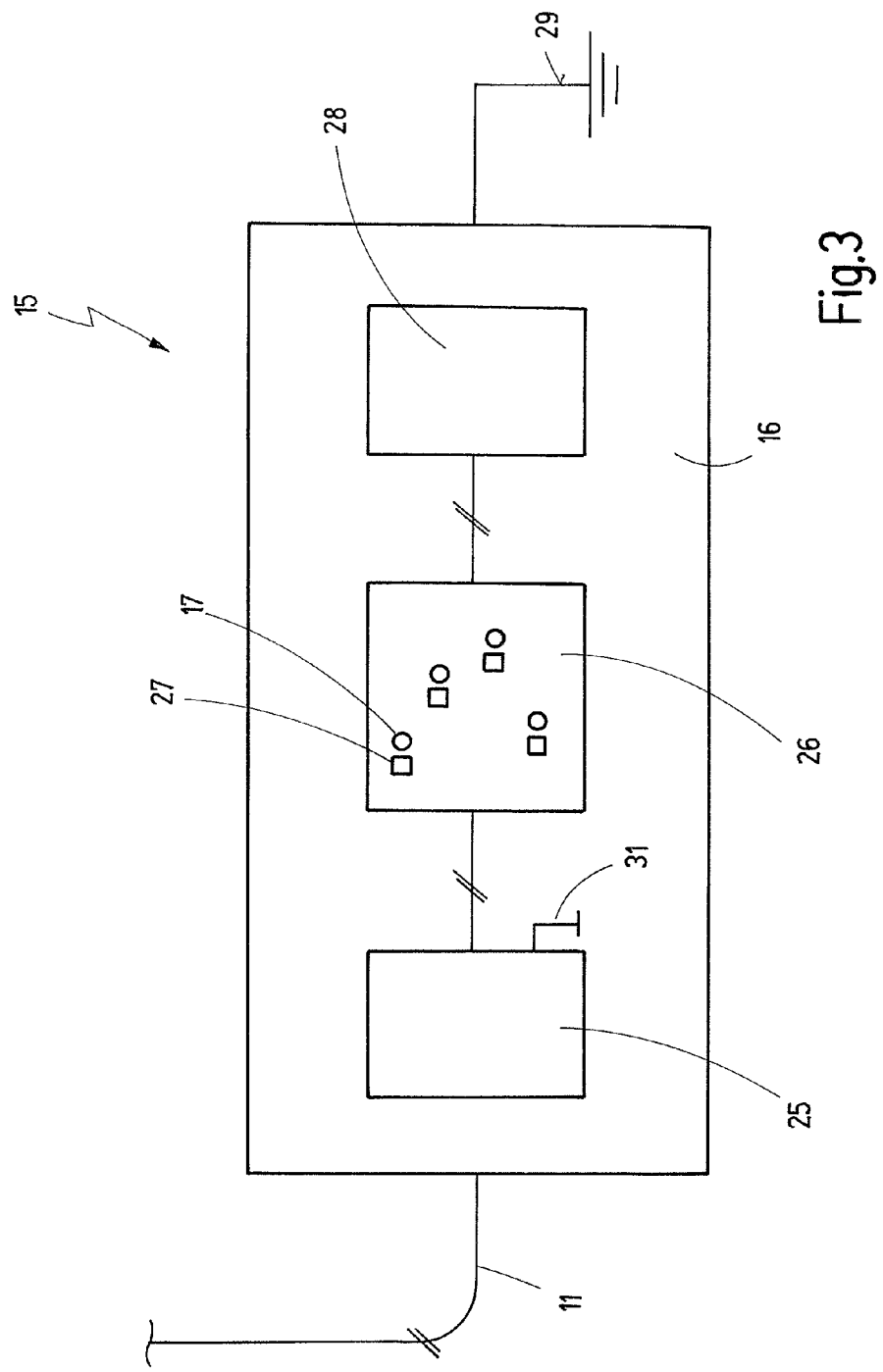
FIG. 3 shows a schematic representation of the retinal implant according to FIG. 1.

FIG. 3 schematically shows the design of the active retinal implant 15 according to FIG. 1. First of all, it is possible to recognize an input stage 25 on the film 16, which input stage is fed external energy from the outside via the cable 11. The input stage 15 is connected to a sensor unit 26 which in this case has a multiplicity of picture cells 27, which convert the incident visible light into electrical signals, which are then emitted to the nerve cells of the retina by the stimulation electrodes 17 indicated next to the respective picture cells.

An output stage 28 processes the useful signals generated by the picture cells 27 and generates the corresponding stimulation signals which are then led back to the sensor unit 26 or the stimulation electrodes 17.

It should be mentioned in this context that FIG. 3 is only a schematic illustration of the retinal implant 15 which reproduces the logical design; the actual geometric arrangement of the individual components can lead, for example, to each picture cell 27 having an output stage in its direct vicinity.

The implant 15 is connected to the tissue into which it is inserted by an external ground, indicated at 29. Furthermore, another electrical ground 31 is indicated, which, in the embodiment shown, is not connected to the external ground 29.

Figure 4:
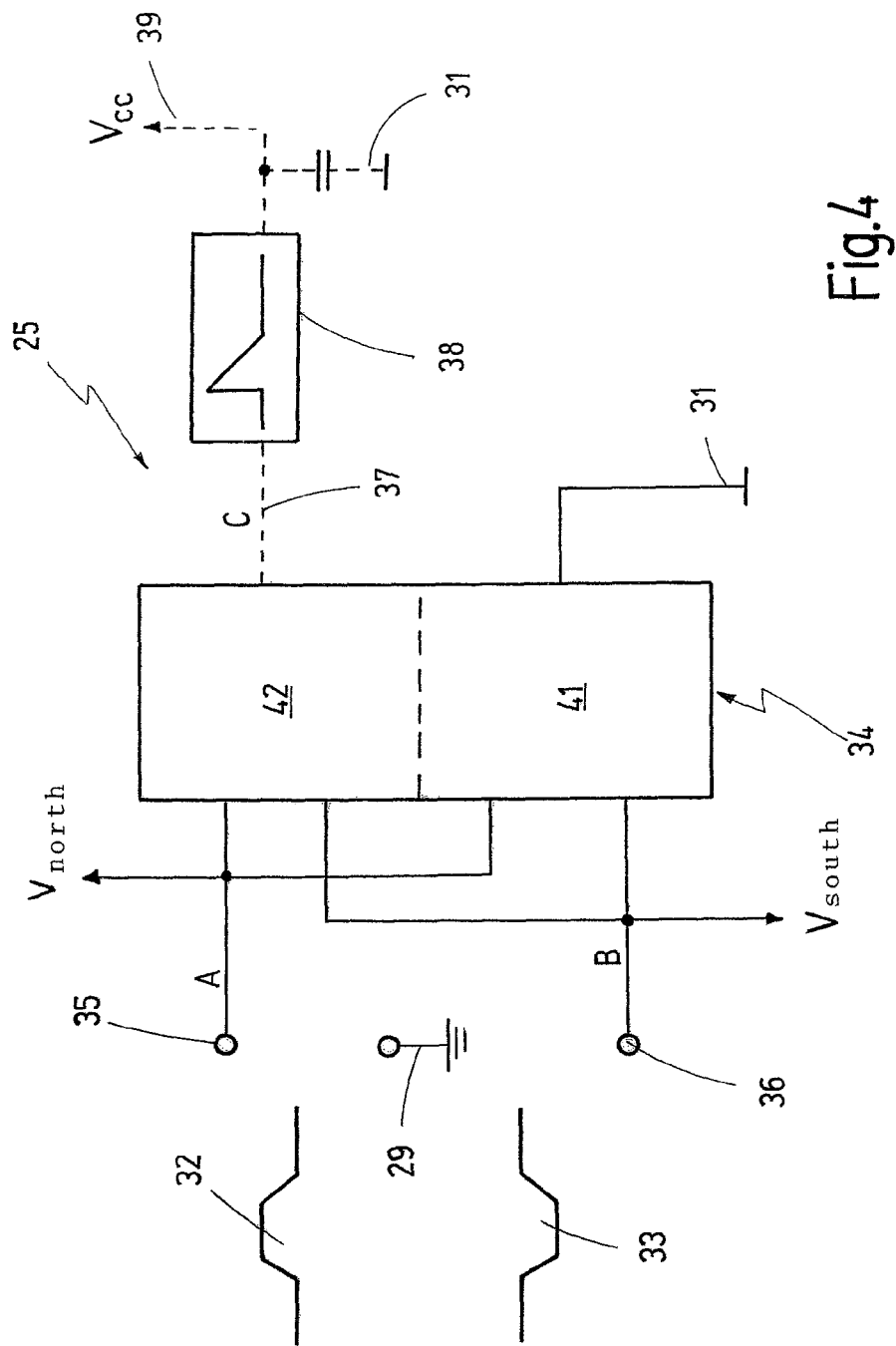
FIG. 4 shows a schematic representation of the input stage of the retinal implant according to FIG. 3.

FIG. 4 shows the input stage 25 of the implant 15 according to FIG. 3 in more detail.

First of all, it can be seen that respectively two square AC voltages 32, 33 are fed in via the cable, which voltages have an inverted profile, i.e., their phases are shifted by 180° with respect to one another, and which voltages are symmetric with respect to the external ground 29 so that, averaged over time, they represent a DC voltage free supply for the implant.

These two AC voltages 32, 33 enter a rectifier circuit 24 by being led to the two inputs 35 and 36. At its output 37, the rectifier circuit 34 is provided with a switch 38 which emits the DC supply voltage indicated at 39. A capacitor is also illustrated to electrical ground 31 in a dashed fashion, whereby this capacitor not necessarily is provided as a separate component; rather it can, for example, represent the input capacitances of the downstream integrated circuit components.

The rectifier circuit 34 has a first branch 41, which is connected to the electrical ground 31 at its output, and a second branch 42, which provides the DC supply voltage 39 via the output 37.

Figure 5:
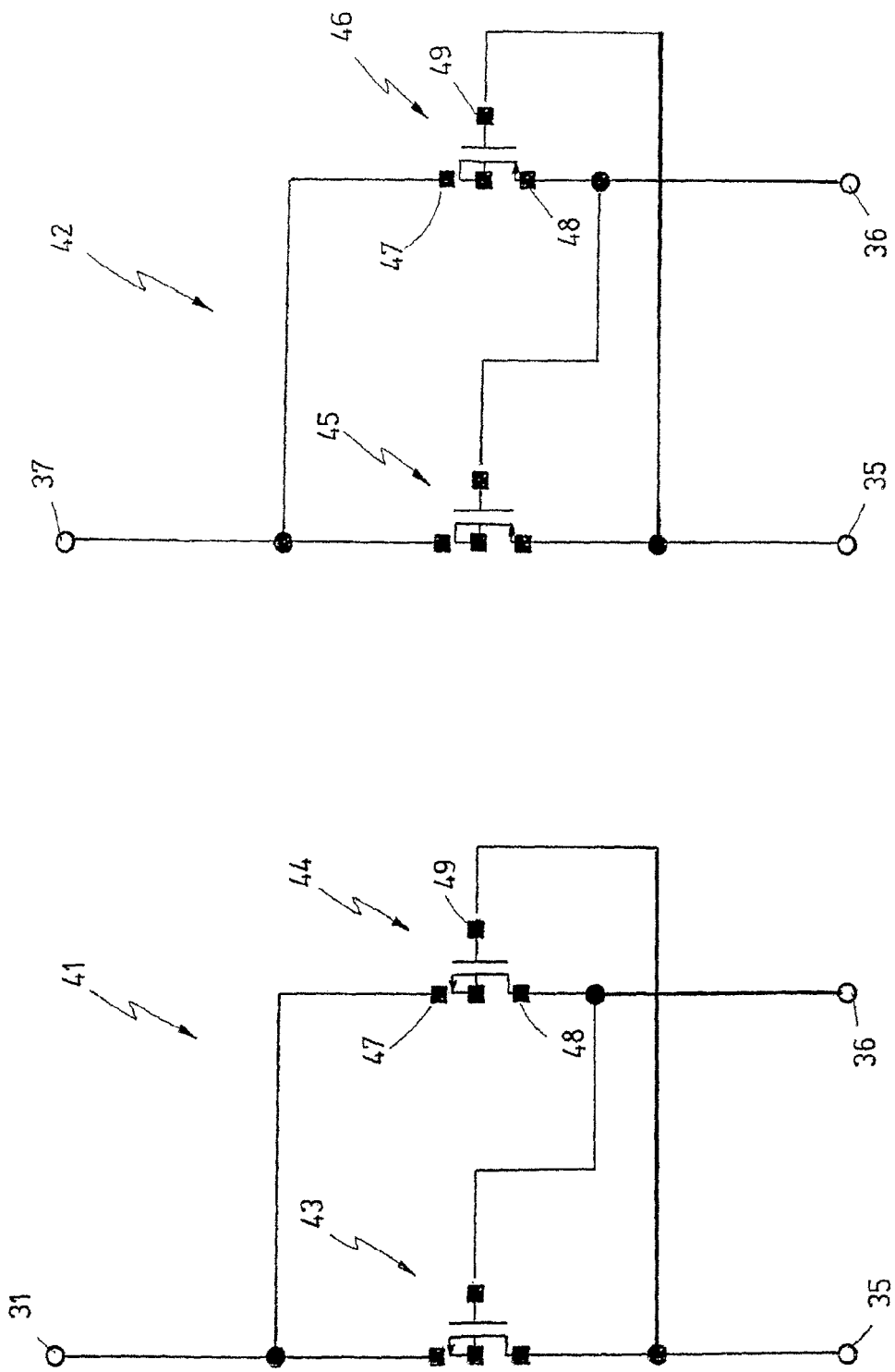
FIG. 5 shows a schematic representation of the two branches of the rectifier circuit of the input stage according to FIG. 4.

The design of the two branches 41 and 42 of the rectifier circuit 34 is shown in detail in FIG. 5.

The first branch 41 has two n-MOS field-effect transistors 43, 44, while two p-MOS field-effect transistors 45, 46 are provided on the second branch 42.

Two field-effect transistors 43, 44 or 45, 46 are connected in parallel at their output electrode 47 in each of the two branches 41 and 42, with the first square AC voltage 32 being connected to the input electrodes 48 one time, and the second square AC voltage 33 being connected at another time. The AC voltage connected to the input electrode 48 of the respective other field-effect transistor in the respective branch is connected to the control electrode 49.

In this fashion, the field-effect transistors 43 and 44 are for example always connected through when the AC currents 32 (at connector 35) or 33 (at connector 36) emit a negative pulse and the respective other AC voltage correspondingly emits a positive pulse which is fed to the control electrodes 49.

In other words, this means that the negative pulses are in each case available at connector 31 and the positive pulses are in each case available at the connector 37, so that the DC supply voltage at connector 37 has a signal level with respect to connector 31 which corresponds to the sum of the positive and negative amplitudes of the AC voltages. The selected circuit furthermore provides for the external ground 29 to lie symmetrically between the electrical ground 31 and the DC supply voltage 37.

Figure 7:
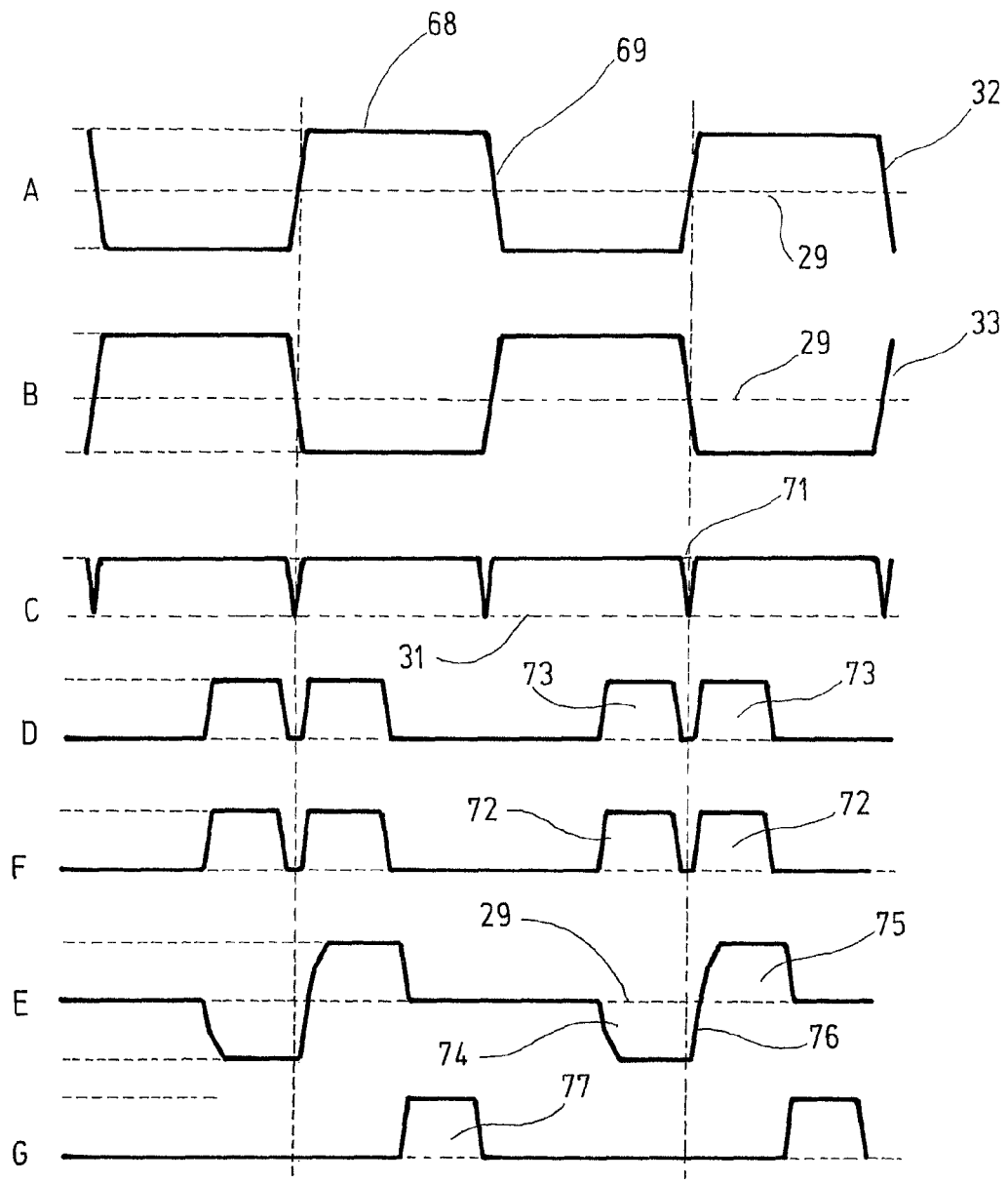
FIG. 7 shows a schematic representation of different control signals and signal forms in the input stage according to FIG. 4 and in the sensor unit and output stage according to FIG. 6.

The resultant curve profiles can be seen in FIG. 7, with A and B showing the AC voltages 32 and 33, while C shows the signal available at output 37 in FIG. 3.

Figure 6:
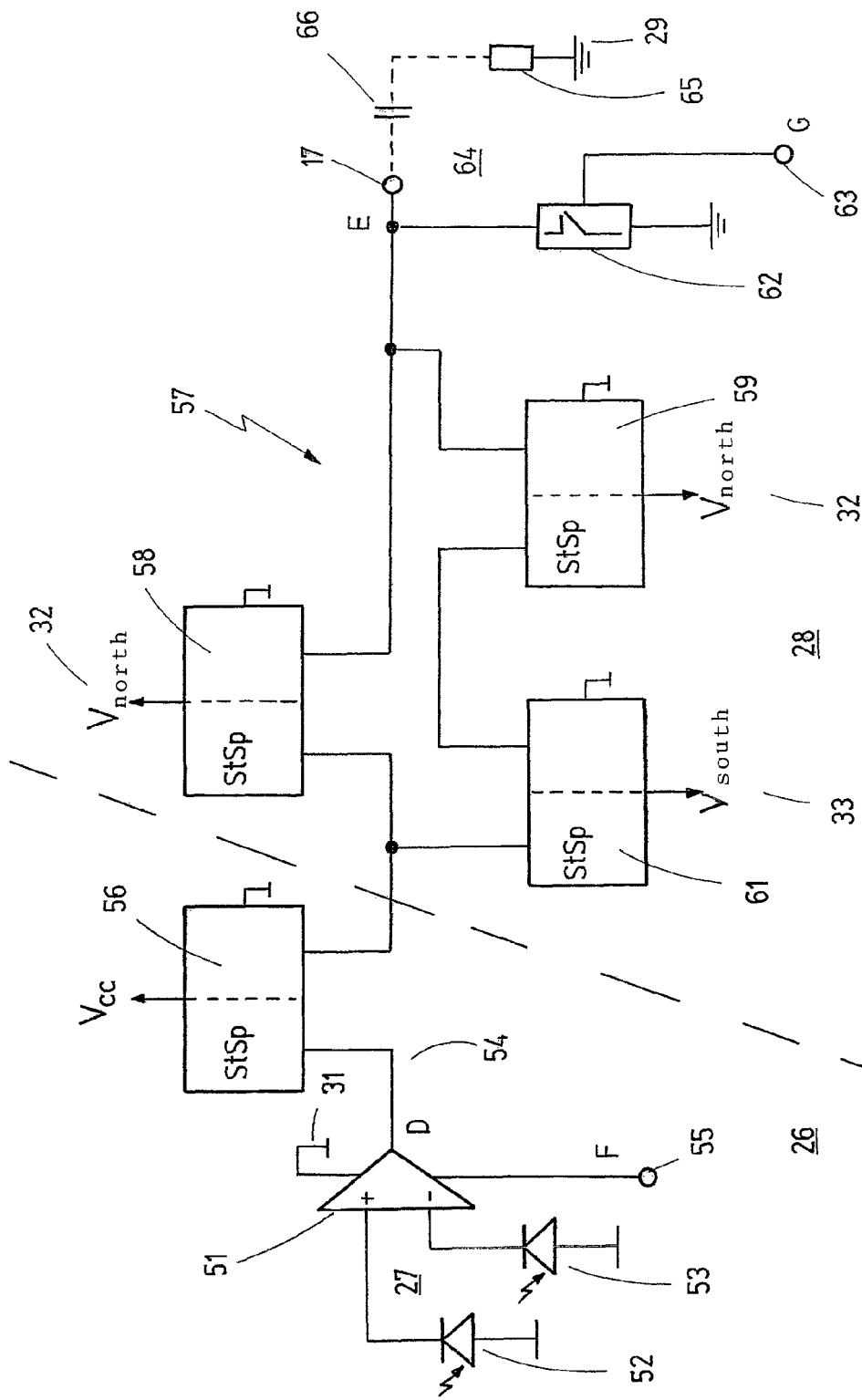
FIG. 6 shows a schematic representation of the sensor unit and the output stage of the retinal implant according to FIG. 3.

FIG. 6 now schematically shows the sensor unit 26 and the output stage 28 of the implant 15, connected thereto, according to FIG. 3. For the sake of simplicity, FIG. 6 only illustrates one picture cell 27 which is only assigned a single output stage 28. In the illustration, the stimulation electrode 17 is located to the right of the output stage 28; however, in the actual geometric arrangement, the stimulation electrode 17 can be arranged next to or in the picture cell 27.

The picture cell 27 now has at its output an output amplifier 51 which is connected to a photodiode 52 for local brightness and a further photodiode 53 for global brightness. In this fashion, the amplifier 51 outputs a signal D at its output 54, the amplitude of which corresponds to the brightness of the light incident on the local photodiode 52, albeit corrected by the global brightness (photodiode 53). The precise design of a picture cell is analogous to those picture cells described in WO 2005/000395 A1, so reference may be made to this document for further information.

At its input 55, the output amplifier 51 is also connected to a control signal F by means of which the output signal D at the output 54 can be clocked in a fashion which will be described below.

The output amplifier 51 is followed by an output current mirror 56 which mirrors the current flowing in to the output amplifier 51 and hence simultaneously also guides this current to an inverter 57 provided in the output stage 28.

The inverter 57 has two current mirrors 58, 59 which are connected to the first AC voltage 32 and are connected to the stimulation electrode 17 at their output. A further current mirror 61 is provided in the lower branch of the inverter 57, with said current mirror being connected to the DC supply voltage 33 and connected between the picture cell 27 and the current mirror 59.

The inverter 57 which is designed in this fashion ensures that, in a fashion which will be described below, the polarity of the current pulses D reverses at the same time as the phase change of the AC voltages 32, 33 so that, averaged over time, the stimulation signals E supplied at the stimulation electrode 17 are DC voltage free.

A switch 62, which connects the stimulation electrode 17 to the external ground 29, is also connected to the stimulation electrode 17 and is actuated by a control signal G provided at the connector 63.

A tissue 64, which can be the recipient of stimulation signals E, is also illustrated schematically. Here, a series circuit comprising an ohmic resistor 65 and a capacitor 66 is selected as an electrical equivalent circuit diagram, representing the Helmholtz double layer formed as a result of the electrode polarization.

Hence, the retinal implant 15 described in so far is firstly supplied, averaged over time, in a DC voltage free fashion by means of the AC voltages 32, 33, whereby it secondly emits to the surrounding tissue an excitation signal E which, averaged over time, is likewise DC voltage free.

Moreover, the retinal implant 15 also requires the control signals F for switching the useful signal D and the control signal G for switching the stimulation signal E. On the one hand, these signals can be derived on the chip from the AC voltages 32 and 33, with, on the other hand, it also being possible to likewise supply said signals by means of the cable 11, that is in separate lines.

If the voltage levels of these control signals remain below 0.3 V, then additionally there is no risk of electrolytic decay and it is possible to use the control signals for controlling the current. To this end, the control signals can be coupled into the retinal implant 15 by a separate input circuit which causes a small input impedance and supplies a high-resistance output by means of which different loads can be fed in. This makes it possible to supply the control signals from the outside without the risk of electrolytic decay.

The same is true for the signal of the global photodiode 52 which is used in a known fashion to adjust the signal to the surrounding or ambient brightness. In the process, this signal for the surrounding brightness can either be generated on the chip itself, as described in WO 2005/000395 A1, or the signal can also be supplied from the outside by means of a separate cable as described above.

The current flowing from the output current mirror 56 and into the output amplifier 51 as a result of the useful signal D is now likewise mirrored in the inverter 57, and said current either flows into the current mirror 58 or the current mirror 61 because at the time only one of these two current mirrors is connected to an AC voltage exhibiting a negative pulse. The DC supply voltage 39 (Vcc) is at +1.5 V and, by contrast, the electrical ground 31 is at −1.5 V with respect to the external ground 29. Thus, if the AC voltage 33 exhibits the negative pulse, the current mirror 61 is pulled to −1.5 V and so the current flows from the output current mirror 56 into the current mirror 61. The mirrored current from the current mirror 59 simultaneously flows in this current mirror 61 because it is connected to the other AC voltage 32, the positive pulse of which is likewise +1.5 V. This current is mirrored again and hence flows from the current mirror 59 into the external ground 29.

If the polarities of the AC voltages 32, 33 now change, the mirrored current of the current mirror 56 flows into the current mirror 58 because the AC voltage 32 now lies at −1.5 V. Now, current from the external ground 29 likewise flows in this current mirror 58 and so the current flow through the capacitor 66 is reversed.

The overall operation sequence of the implant described in so far is now intended to be described based on FIG. 7 and with reference to FIGS. 4 and 6.

As mentioned above, two AC voltages 32 and 33, having a trapezoidal profile in time and respectively lying symmetrically with respect to the external ground 29, are fed to the implant 15. Moreover, the two AC voltages 32 and 33 are inverted with respect to one another, that is to say they have a phase-shift of 180° with respect to one another.

The individual voltage pulses have a top phase 68 of, e.g., 20 ms and a pulse-edge phase 69 of, e.g., 1 ms. Although shorter pulse-edge phases are possible, pulse-edge phases which are too short could possibly lead to radiofrequency interference and this is why, from an electronics point of view, relatively long pulse-edge phases are selected.

After rectification by switches provided in the branches 41 and 42, the voltage C at output 37 has a pulsed profile; the voltage collapses in each phase change and this is illustrated by a voltage drop 71. This voltage drop 71 results from the use of field-effect transistors 43, 44, 45, 46, whereas conventional rectifier diodes in a bridge circuit would not force this voltage drop.

In principle, the downstream components in the respective circuit could cope with this voltage drop, with it being possible that provision is additionally made for the switch 38 to separate the output 37 from the DC supply voltage 39 during the voltage drops 71 so that said voltage can remain constant.

The useful signal D emitted by the output amplifier 51 follows, seen from the top, in FIG. 7. The picture cell 27 first of all generates a long pulse, the amplitude of its intensity corresponding to the light incident on the photodiode 52.

However, this output signal is now not emitted as a continuous pulse; rather the amplifier 51 is clocked by the control signal F having two control pulses 72 which are symmetric with respect to the pulse edges 59.

In this fashion, the useful signal D is also subdivided into two voltage pulses 73 which are symmetric with respect to the pulse edges of the AC voltages 32, 33.

The inverter 57 now, at the same time mirrors the first of the two pulses 73, resulting in the stimulation signal E, which comprises a cathodic preparation pulse 74 and an anodic excitation pulse 75 with respect to in each case the external ground 29. That is to say, the stimulation signal E is a biphasic excitation for the surrounding tissue 64, with the excitation commencing with a cathodic pulse. This makes a larger pulse edge 76 available to the excitation signal and briefly leads to a high current flow into the surrounding tissue 64, so that a good excitation of the downstream nerve cells is achieved.

In order to now ensure that on average there is no charge shift into the tissue 64, the switch 62 is briefly closed by the control signal G after the pulse sequence 74, 75 is completed so that the capacitor 66 discharges. Thereby, it is important that the switch 62 connects with the external ground 29.

Thus, in this fashion, the stimulation signal E is, on the one hand and averaged over time, DC voltage free, with it on the other hand being ensured that all the charge which flowed into the tissue is returned, so that a renewed excitation can be undertaken with the subsequent useful signal D.

Therefore, what is claimed is:

1. Implantable device, comprising
    at least one stimulation electrode for emitting electrical stimulation signals to surrounding tissue,
    an external ground to be connected to the tissue,
    a sensor unit, which generates, from externally fed signals, a useful signal (D) in the form of analogue voltage pulses,
    an output stage, which generates the stimulation signals from the useful signal, and
    an input stage for providing a DC supply voltage and an electrical ground which are substantially symmetric with respect to the external ground, wherein the output stage emits the stimulation signals to the external ground without a DC offset voltage.

2. The Device of claim 1, wherein the output stage comprises an inverter which supplies the stimulation signals to the stimulation electrode as a sequence of pulses which respectively have two different phases.

3. The Device of claim 2, wherein the inverter has two branches, connected in parallel to one another, between the output of the sensor unit and the stimulation electrode.

4. The Device of claim 3, wherein both branches respectively comprise at their output a first current mirror connected to a first AC voltage.

5. The Device of claim 4, wherein the one branch comprises a second current mirror, connected to a second AC voltage, which second current mirror is connected between the sensor unit and the first current mirror.

6. The Device of claim 2, wherein the inverter reverses the polarity of the voltage pulses with respect to the external ground synchronously with AC supply voltages.

7. The Device of claim 1, comprising
    an input stage, and
    a supply unit for supplying the device with electrical energy, said supply unit being connected to the device via cables and supplying said input stage with at least one substantially square electrical AC voltage,
    said AC voltage being, averaged over time, at least virtually free of a DC voltage with respect to the external ground.

8. The Device of claim 7, wherein the supply unit supplies the input stage with at least two substantially square electrical AC voltages, which are, averaged over time, at least virtually free of a DC voltage with respect to the external ground.

9. The Device of claim 8, wherein said AC voltages are phase-shifted with respect to one another.

10. The Device of claim 8, wherein the input stage comprises a rectifier circuit, which rectifies the AC voltages and adds them to form a DC supply voltage.

11. The Device of claim 9, wherein the input stage is supplied with a first and a second AC voltage which, while exhibiting approximately the same curve profile and approximately the same amplitudes, are at least virtually inverted with respect to one another.

12. The Device of claim 10, wherein the rectifier circuit generates the DC supply voltage from the first and the second AC voltages such that the electrical ground thereof and the DC supply voltage are symmetric with respect to the external ground.

13. The Device of claim 10, wherein the rectifier circuit has switches for the respective AC voltage which are actuated by the respective other AC voltage.

14. The Device of claim 10, wherein the rectifier circuit comprises two branches with respectively two field-effect transistors connected in parallel at their output electrodes.

15. The Device of claim 14, wherein the output electrodes in the first branch form the electrical ground and the output electrodes in the second branch emit the DC supply voltage.

16. The Device of claim 14, wherein every field-effect transistor is connected to one of the two AC voltages at its input electrode and is connected to the other one of the two AC voltages at its control electrode.

17. The Device of claim 15, wherein the output of the second branch is connected to the DC supply voltage via a switch.

18. The Device of claim 17, wherein the switch is always open when the AC voltages change their polarity with respect to the external ground.

19. The Device of claim 8, wherein the or every AC voltage has a trapezoidal voltage profile with top phases of constant voltage and short pulse-edge phases in which the polarity with respect to the external ground changes.

20. The Device of claim 19, wherein the duration of the top phases is of the order of at most 100 ms.

21. The Device of claim 19, wherein the pulse-edge phases are at most 10%, preferably being less than 1% but more than 0.05% of the top phase.

22. The Device of claim 5, wherein the sensor unit has an output amplifier at its output.

23. The Device of claim 22, wherein the output of the output amplifier is always switched off by means of a control signal when the AC voltages change their polarity with respect to the external ground.

24. The Device of claim 2, wherein the inverter has a switch at its output, which always briefly connects the output to the external ground when a voltage pulse is over, the amplitude of which thus being connected to the internal ground for the duration of the pulse spacing.

25. Implantable device according to claim 1, wherein said sensor unit comprises a multiplicity of image cells which convert incident light into electrical signals, said sensor unit using the electrical signals to generate said useful signal in the form of analog voltage pulses of a certain pulse duration and certain pulse spacing, the amplitudes of which depending on the respective intensity of the incident light.

26. Active retinal implant, comprising
    a sensor unit, comprising a multiplicity of image cells which convert incident light into electrical signals,
    said sensor unit using the electrical signals to generate a useful signal in the form of analogue voltage pulses of a certain pulse duration and certain pulse spacing, the amplitudes of which depending on the respective intensity of the incident light, at least one stimulation electrode for emitting electrical stimulation signals to surrounding tissue, an external ground to be connected to the tissue, an output stage, which generates the stimulation signals from the useful signal and emits the stimulation signals to the external ground in, averaged over time, a substantially DC voltage free fashion, and a DC supply voltage and an electrical ground which are substantially symmetric with respect to the external ground.

27. The Active retinal implant of claim 26, wherein the output stage comprises an inverter which supplies the stimulation signals to the stimulation electrode as a sequence of pulses which respectively have two different phases.

28. The Active retinal implant of claim 27, wherein the inverter has two branches, connected in parallel to one another, between the output of the sensor unit and the stimulation electrode.

29. The Active retinal implant of claim 28, wherein both branches respectively comprise at their output a first current minor connected to a first AC voltage.

30. The Active retinal implant of claim 29, wherein the one branch comprises a second current mirror, connected to a second AC voltage, which second current mirror is connected between the sensor unit and the first current minor.

31. The Active retinal implant of claim 27, wherein the inverter reverses the polarity of the voltage pulses with respect to the external ground synchronously with the AC voltages.

32. The Active retinal implant of claim 26, comprising an input stage, and a supply unit for supplying the device with electrical energy, said supply unit being connected to the device via cables and supplying said input stage with at least one substantially square electrical AC voltage, said AC voltage being, averaged over time, at least virtually free of a DC voltage with respect to the external ground.

\* \* \* \* \*